US00PP37343P2

(12) United States Plant Patent
Hansen

(10) Patent No.: US PP37,343 P2
(45) Date of Patent: Mar. 24, 2026

(54) ***HELIOPSIS* PLANT NAMED 'Sunny Disposition'**

(50) Latin Name: ***Heliopsis helianthoides* (L.) Sweet**
Varietal Denomination: Sunny Disposition

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,924

(22) Filed: Nov. 13, 2025

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 5/02
See application file for complete search history.

*Primary Examiner* — Kent L Bell

(57) ABSTRACT

The new and distinct hardy perennial *Heliopsis* plant named 'Sunny Disposition' with dense, rounded, extensively-branched habit, strong, upright stems that resist lodging. A foliage is broadly ovate to narrowly deltoid medium green surrounding veins with a variable amount of white between the veins. Freely-flowering semi-double inflorescences in a capitulum with multiple rows of golden-yellow, overlapping, ray florets and disk florets near the center, beginning in early July and continuing for about 6 to eight weeks. The new plant is useful in the landscape en masse, as an accent, in containers or as cut flowers.

1 Drawing Sheet

Botanical denomination: *Heliopsis helianthoides* (L.) Sweet.

Variety designation: 'Sunny Disposition'.

STATEMENT REGARDING PRIOR DISCLOSURES UNDER 37 CFR 1.77(B)(6)

The first offer for sale of *Heliopsis* 'Sunny Disposition' was to Plants Inc. by Walters Gardens, Inc. on Nov. 25, 2024. Since then, it has also been sold to Mason Hollow Nursery and Prides Corner Farms. Walters Gardens, Inc. obtained the new plant and all information relating thereto, directly from the inventor. No plants of *Heliopsis* 'Sunny Disposition' have been sold, in this country or anywhere in the world, by any name, nor has any disclosure of the new plant been made more than one year prior to the filing date of this application, and such sale or disclosure within one year was either derived directly or indirectly from the inventor and would be a 35 U.S.C. § 102(b) exception.

BACKGROUND AND ORIGIN OF THE PLANT

The present invention relates to a new and distinct cultivar of *Heliopsis* 'Sunny Disposition'. The new plant was selected as a single seedling from the cross by the inventor at a wholesale perennial nursery in Zeeland, Michigan between the unreleased, proprietary hybrid 16-15-1 (not patented) as the female or seed parent and the unreleased, proprietary hybrid 16-7-1 (not patented) as the male or pollen parent on Aug. 9, 2017. Seed was harvested on Nov. 24, 2017, and eventually the individual seedling was assigned the breeder code 17-11-26 during the trial period. 'Sunny Disposition' was approved in an initial evaluation in the summer of 2019 and slated for later introduction. The new plant was selected based on its compact habit, strong stems, ability to withstand lodging, mildew resistance, attractive colorful foliage, high-quality semi-double inflorescences over a long period, and ability to attract pollinators. The new plant has been asexually first propagated at the same perennial wholesale nursery by division in 2019 and later by shoot tip cuttings with the resultant asexually propagated plants remaining identical to the original plant, stable and true to type in successive generations.

SUMMARY OF THE INVENTION

Plants of the new false sunflower have not been observed under all possible combinations of environmental conditions and cultural practices. The phenotype may vary somewhat with variations in environmental conditions comprising temperature, daylength, light intensity, and fertility, without, however, any variations in genotype.

The following traits have been repeatedly observed and are determined to be the unique characteristics of the new *Heliopsis* plant. These characteristics in combination distinguish 'Sunny Disposition' as a new and distinct *Heliopsis* plant:

1. Ovate to deltoid foliage has medium green foliage with white between the veins;
2. Dense rounded plant habit and extensive branching habit;
3. Very floriferous and freely flowering habit beginning in early July and continuing for about six to eight weeks;
4. Semi-double inflorescences with multiple rows of golden-yellow ray florets with a low number of disk florets;
5. Strong garden performance and excellent for cut flowers.

The female parent has a shorter more compact habit with variegated foliage having green surrounding the veins and yellowish cream between the veins, and the inflorescences have fewer ray florets. The male parent has a larger habit with double inflorescences and variegated foliage having green surrounding the veins and yellowish cream between the veins.

The following cultivars are the most similar cultivars known to the inventor: 'Asahi' (not patented), 'Double Sunstruck' U.S. Plant patent application Ser. No. 14/121,359, 'Loraine Sunshine' U.S. Plant Pat. No. 10,690, 'Sunstruck' U.S. Plant Pat. No. 25,524, and 'Touch of Blush' U.S. Plant Pat. No. 36,739.

'Asahi' produces smaller double inflorescences with yellow ray florets and solid green leaves. 'Double Sunstruck' has a shorter habit and more intensely variegated foliage with more white between the veins. 'Loraine Sunshine' has a taller habit, more intensely variegated foliage, and the inflorescences have a single row of ray florets. 'Sunstruck' has much shorter habit, the foliage has more white and less green, and the inflorescences have a single row of ray florets. 'Touch of Blush' has a slightly shorter and more compact habit, the foliage is more variegated with white and touches of purplish-red, and inflorescences have a single row of ray florets that have burnt orange center when young.

BRIEF DESCRIPTION OF THE DRAWINGS

The photographs of the new plant demonstrate the unique traits of *Heliopsis* 'Sunny Disposition' and the overall appearance of a three-year-old plant in the full sun display garden of a nursery in Zeeland, Michigan. The colors are as accurate as reasonably possible with color reproductions. Variation in ambient light spectrum, source and direction may cause the appearance of minor variation in color.

DETAILED BOTANICAL DESCRIPTION

Figure 1:
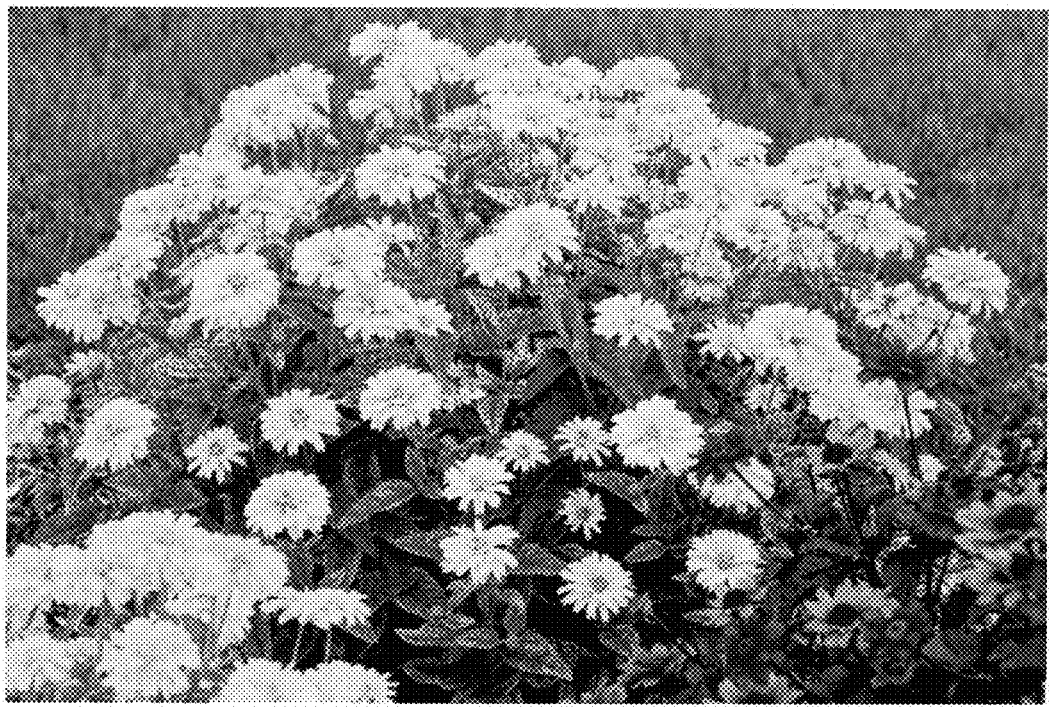
FIG. 1 shows the landscape habit of the new plant in full flower.
Figure 2:
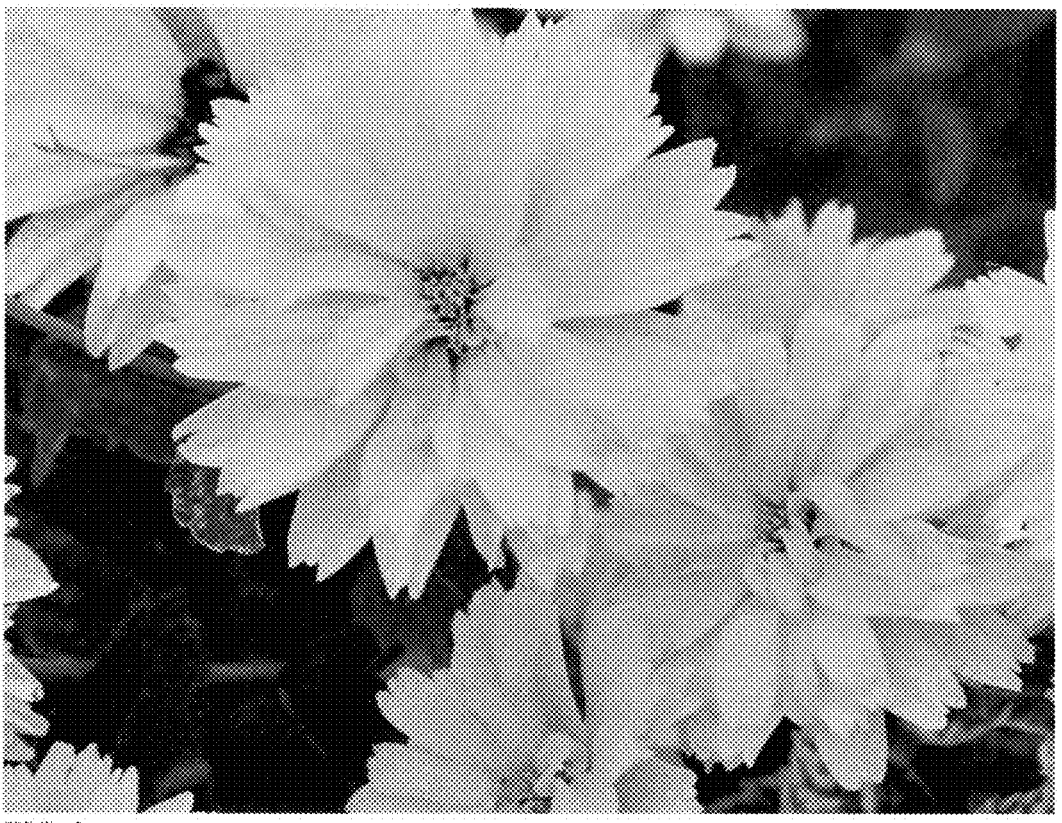
FIG. 2 shows a close-up of some inflorescences.

The following descriptions and color references are based on the 2015 edition of The Royal Horticultural Society Colour Chart except where common dictionary terms are used. *Heliopsis* 'Sunny Disposition' has not been observed in all possible environments. The phenotype may vary slightly with different growing environments such as temperature, light, fertility, soil pH, moisture, and maturity levels, but without any change in the genotype. The following observations and size descriptions are based on three-year-old plants grown in a trial garden at a nursery in Zeeland, Michigan with supplemental fertilizer and water as needed and without growth regulators or pinching.

Botanical classification: *Heliopsis helianthoides;*

Parentage: The female (or seed) parent is 16-15-1; the male (or pollen) parent is 16-7-1;

Plant habit: Multi-stemmed, heavily-branched, herbaceous perennial forming a dense rounded mound;

Propagation: Shoot tip cuttings;

Time to initiate roots: About one to two weeks;

Plant size: To about 78 cm tall and 82 cm wide;

Growth rate: Moderate; about 8 to 12 weeks to finish in a 3.8-liter container from a rooted 25 mm plug liner;

Root description: Fibrous; medium thickness; light tan to white in color, depending on soil composition, water quality, fertilizer type and formulation, substrate temperature, and physiological age of roots; medium density;

Stems: About 120 per plant; cylindrical; sparsely micro-puberulent; to about 63 cm long to terminal peduncle and 6.5 mm diameter at base;

Stem color: Between RHS N144D and RHS 145C;

Branches: About 6 branches per stem beginning about 52 cm above soil; cylindrical; micro-puberulent; strong; stiff; at about a 30-degree angle away from main stem; to about 20 cm long and 2 mm diameter at base; color between RHS N144A and RHS 145D;

Branch aspect: About 60 degrees above the horizon;

Nodes: About 7 below terminal flower; average internode length about 9 cm; node color between RHS 146D and RHS 146C;

Leaf description: Broadly ovate to narrowly deltoid; opposite; apex acute; base slightly oblique and truncate to rounded; margin micro-ciliolate and serrate with about 18 teeth per side; scaberulose adaxial and abaxial;

Leaf size: To about 8 cm long and 5 cm wide, average about 8.5 cm long and 5 cm wide;

Leaf color: Young adaxial between RHS 137A and RHS 137B, young abaxial between RHS 147B and RHS 147C; mature flowering stage adaxial nearest RHS NN137B, abaxial between RHS 146D and RHS 147C;

Veins: Reticulate; slightly recessed and glabrous adaxial, abaxial costate and micro-puberulent to scaberulose;

Vein color: Young adaxial midrib and primary veins between RHS 145B and RHS 146D and secondary veins nearest RHS 137C, abaxial midrib and primary veins nearest RHS 147C and secondary veins nearest RHS 137A; mature adaxial midrib and primary veins nearest RHS N179C and secondary veins nearest RHS 146D; mature abaxial midrib and primary veins between RHS 146D and RHS 145C and secondary veins nearest RHS 137B;

Petioles: Concavo-convex; sparsely puberulent adaxial and abaxial; to about 22 mm long and 5 mm across at base;

Petiole color: Adaxial between RHS 146D and RHS 144D and abaxial between RHS 146D and RHS 145A;

Inflorescence: In terminal capitulum; inflorescences semi-double with disk florets in the center and 80 to 90 ray florets in four to six layers surrounding about 30 disk florets; to about 24inflorescences per stem;

Flowering season: Begins in early July and continues for about six weeks;

Inflorescence buds: Tubular with flat top and rounded base; with ray florets still upright about 25 mm tall and 3.5 cm across;

Bud color: Ray florets nearest RHS 17C with an undertone of nearest RHS 144B;

Inflorescence longevity: Lasting about seven to ten days on the plant or as a cut flower; persistent;

Fragrance: Very slight, sweet;

Inflorescence size: To about 8.2 cm across and 4.5 cm tall;

Disk receptacle: Obconical with acute apex and flat base, about 10 mm across and 7 mm tall in maturity;

Receptacle color: Nearest RHS 155B as developing and nearest RHS 197C at maturity;

Ray florets: Ligulate; pistillate; about 80 to 90 ray florets in four to six imbricate whorls; lanceolate with emarginate apex indented with two notches to about 2 mm to 4 mm; base attenuate; margin entire; adaxial and abaxial surface glabrous and matte; with typically two longitudinal furrows; aspect outer whorls arcuate downward, and inner whorls horizontal to slightly upwardly when mature;

*Size*.—To about 35 mm long and 8 mm across near middle.

*Ray floret color*.—Upon initially becoming flat-adaxial base nearest RHS 14A and distally nearest RHS 14A, abaxial nearest RHS 13B; near the final stage of effective inflorescence adaxial nearest RHS 14A, abaxial nearest RHS 14B.

Disk florets: About 30 per inflorescence; tubular; anthers and style exserted;

*Size*.—To about 7 mm long and 3 mm wide at exserted style.

*Corolla tube*.—Five indistinguishable perianth or tepals; to about 5 mm long and 3 mm across at apex.

*Tepals*.—Acute apex; connate in proximal 4.5 mm; margin entire; glabrous; slightly lustrous adaxial and abaxial; to about 5 mm long and about 0.7 mm across at fusion; color apex adaxial and abaxial distally nearest RHS N25A; adaxial and abaxial proximally nearest RHS 145D.

Reproductive organs: Ray florets: anandrous;

*Gynoecium*.—To 8 mm long; exserted.

*Style*.—Cylindrical; to about 3 mm long and 0.2 mm diameter; color nearest RHS 17C.

*Stigma*.—Bifid in distal 2 mm; color nearest RHS 17B.

*Ovary*.—Obconical; about 1 mm long and 0.7 mm diameter at apex and about 0.5 mm diameter at base; color between RHS 145D and 145C.

Reproductive organs: Disk florets: perfect;

*Gynoecium*.—To 7 mm long; exserted.

*Style*.—Cylindrical; to about 2.5 mm long and 0.2 mm diameter; color nearest RHS 17C.

*Stigma*.—Bifid in distal 2 mm; color nearest RHS 17B.

*Ovary*.—About 1 mm long and 0.7 mm across; color between RHS 157D and RHS 156D.

*Androecium*.—Connate; to about 5 mm long.

*Anthers*.—Five; synandrous; introrse; basifixed; tube to about 2 mm long and 0.5 mm diameter; color between RHS N199A and RHS 199A.

*Filaments*.—Five; to about 3 mm long and 0.1 mm diameter; color nearest RHS 155C.

*Pollen*.—Abundant; color nearest RHS N25B.

Seeds: Achene; apex truncate; base acute; surface smooth, glabrous, matte; angular distally; to about 3 mm long and 1.5 mm across at apex; about 70 per inflorescence; color nearest RHS N199B;

Flowering period: In Western Michigan beginning early July for about six to eight weeks; individual florets remain open for about 4 to 6 days;

Flower attitude: Upwardly;

Phyllaries: About 21 per inflorescence in two whorls; lanceolate; acute apex; margin entire; puberulent and matte adaxial and abaxial; to about 9 mm long and 4 mm across at base;

Phyllary color: Adaxial between RHS N137B and RHS 137A; abaxial between RHS 146A and RHS 137B;

Peduncles: Cylindrical; micro-puberulent; strong; stiff; upright; to about 10.5 cm long, 4 mm diameter proximally, and 5 mm diameter at the base of the inflorescence;

Peduncle color: Nearest RHS 146D;

Growth: The new plant has been observed to have good garden performance and tolerance to high winds and strong rains.

Hardiness: Winter hardy in USDA zones 4 to 9;

Pest and disease susceptibility: Shows resistance to powdery mildew (*Neoerysiphe galeopsidis*) but no other resistance or susceptibility has been observed beyond that which is typical for *Heliopsis*.

I claim:

1. A new and distinct hardy perennial *Heliopsis* plant named 'Sunny Disposition' substantially as herein described and illustrated.

* * * * *